(12) United States Patent
Mäurer et al.

(10) Patent No.: US 8,779,212 B2
(45) Date of Patent: Jul. 15, 2014

(54) USE OF A SUPPORTED CATALYST CONTAINING PRECIOUS METAL FOR OXIDATIVE DEHYDROGENATION

(75) Inventors: Torsten Mäurer, Lambsheim (DE);
Georg Seeber, Lambsheim (DE);
Radwan Abdallah, Ludwigshafen (DE);
Thorsten Johann, Limburgerhof (DE);
Günter Wegner, Römerberg (DE)

(73) Assignee: BASF SE (DE)

( * ) Notice: Subject to any disclaimer, the term of this patent is extended or adjusted under 35 U.S.C. 154(b) by 87 days.

(21) Appl. No.: 12/933,441

(22) PCT Filed: Mar. 16, 2009

(86) PCT No.: PCT/EP2009/053081
§ 371 (c)(1),
(2), (4) Date: Sep. 20, 2010

(87) PCT Pub. No.: WO2009/115492
PCT Pub. Date: Sep. 24, 2009

(65) Prior Publication Data
US 2011/0015446 A1    Jan. 20, 2011

(30) Foreign Application Priority Data
Mar. 19, 2008 (DE) .......... 10 2008 014 910

(51) Int. Cl.
*C07C 45/29* (2006.01)
*B01J 23/50* (2006.01)

(52) U.S. Cl.
USPC ............ 568/471; 568/473; 568/489; 502/243

(58) Field of Classification Search
USPC .......................... 568/471, 473, 489; 502/243
See application file for complete search history.

(56) References Cited

U.S. PATENT DOCUMENTS

| | | |
|---|---|---|
| 3,697,580 A | 10/1972 | Overwien et al. |
| 4,007,135 A | 2/1977 | Hayden et al. |
| 4,110,403 A | 8/1978 | Ichikawa et al. |
| 4,117,016 A | 9/1978 | Hughes |
| 4,154,762 A | 5/1979 | Huang et al. |
| 4,165,342 A | 8/1979 | Dudeck et al. |
| 4,310,709 A | 1/1982 | Rebafka |
| 4,324,699 A | 4/1982 | Mross et al. |
| 4,732,918 A | 3/1988 | Lohmueller et al. |
| 5,149,884 A | 9/1992 | Brenner et al. |
| 6,013,843 A | 1/2000 | Aquila et al. |
| 6,211,114 B1 | 4/2001 | Brocker et al. |
| 2006/0036106 A1 | 2/2006 | Mazanec et al. |

FOREIGN PATENT DOCUMENTS

| | | |
|---|---|---|
| DE | 1901709 | 8/1970 |
| DE | 2020865 A1 | 11/1971 |
| DE | 2041976 | 3/1972 |
| DE | 2300512 | 7/1973 |
| DE | 2454972 | 6/1975 |
| DE | 2521906 | 12/1975 |
| DE | 2517859 | 3/1976 |
| DE | 2715209 A1 | 10/1978 |
| DE | 2751766 | 5/1979 |
| DE | 2753359 | 6/1979 |
| DE | 3414717 | 10/1985 |
| EP | 0011356 | 5/1980 |
| EP | 0014457 | 8/1980 |
| EP | 0082609 | 6/1983 |
| EP | 0085237 | 8/1983 |
| EP | 0112261 | 6/1984 |
| EP | 0172565 | 2/1986 |
| EP | 244632 A2 | 11/1987 |
| EP | 0266015 | 5/1988 |
| EP | 0339748 | 11/1989 |
| EP | 357292 A1 | 3/1990 |
| EP | 0357293 A1 | 3/1990 |
| EP | 0415745 A2 | 3/1991 |
| EP | 841090 | 5/1998 |
| EP | 0881206 A1 | 12/1998 |
| GB | 1338698 A | 11/1973 |
| GB | 1413251 | 11/1975 |
| GB | 1512625 | 6/1978 |
| JP | 8268939 | 10/1996 |
| WO | WO-01/96324 | 12/2001 |
| WO | WO-02/18042 | 3/2002 |
| WO | WO-03/044003 | 5/2003 |
| WO | WO-2004/002971 | 1/2004 |
| WO | WO-2004/030813 | 4/2004 |
| WO | WO-2008/037693 | 4/2008 |
| WO | WO-2008/098774 | 8/2008 |

OTHER PUBLICATIONS

U.S. Appl. No. 12/297,895, filed Oct. 21, 2008, Mäurer et al.
U.S. Appl. No. 12/920,139, filed Aug. 30, 2010, Limbach et al.
U.S. Appl. No. 12/920,150, filed Aug. 30, 2010, Limbach et al.
Abad, A., et al., "Catalyst parameters determining activity and selectivity of supported gold nanoparticles for the aerobic oxidation of alcohols: the molecular reaction mechanisn," Chem. Eur. J. 2008, vol. 14, pp. 212-222.
Abad, A., et al., "Unique gold chemoselectivity for the aerobic oxidation of allylic alcohols," Chem. Commun. 2006, pp. 3178-3180.

*Primary Examiner* — Sikarl Witherspoon
(74) *Attorney, Agent, or Firm* — Drinker Biddle & Reath LLP

(57) ABSTRACT

The use of a supported noble metal catalyst obtainable by applying a sparingly soluble noble metal compound to a support from solution or suspension, and subsequently treating thermally, for preparing olefinically unsaturated carbonyl compounds.

12 Claims, 2 Drawing Sheets

USE OF A SUPPORTED CATALYST CONTAINING PRECIOUS METAL FOR OXIDATIVE DEHYDROGENATION

CROSS-REFERENCE TO RELATED APPLICATIONS

This application is a national stage application (under 35 U.S.C. §371) of PCT/EP2009/053081, filed Mar. 16, 2009. The present application claims the priority of DE 10 2008 014 910.1. The priority document is incorporated by reference in its entirety into the present disclosure.

BACKGROUND OF THE INVENTION

The present invention relates to the use of a supported noble metal catalyst for preparing olefinically unsaturated carbonyl compounds from olefinically unsaturated alcohols by oxidative dehydrogenation, and to corresponding supported noble metal is catalysts.

More particularly, the present invention relates to the use of supported noble metal catalysts obtainable by a particular process for preparing 3-methylbut-2-en-1-al from 3-methylbut-3-en-1-ol.

The preparation of alpha,beta-unsaturated carbonyl compounds by oxidative dehydrogenation over suitable catalysts is known to those skilled in the art and has been described many times in the literature.

DE-B-20 20 865 accordingly describes a process for preparing alpha,beta-unsaturated carbonyl compounds, wherein the dehydrogenation catalysts used, according to the description, may be alloys and metal compounds, specifically some metal oxides of the transition group elements. It is additionally stated in this document that the catalysts can be used in pure form, such as in the form of mixed catalysts with or without support substance. Particularly suitable catalysts mentioned are zinc oxide, cadmium oxide and manganese oxide, and also mixed catalysts composed of the metals Cu, Ag and/or Zn. Regarding the preparation of the catalyst, there is no further information in this document.

EP-A 881 206 describes a process for continuous industrial preparation of unsaturated aliphatic aldehydes in a tube bundle reactor. Preferred catalysts mentioned for this process are supported silver catalysts which consist of spheres of an inert support material coated with 0.1 to 20% by weight, based on the amount of the support, of a layer of metallic silver in the form of a smooth, abrasion-resistant shell. In addition, a particular ratio of the greatest diameter of the coated catalyst spheres to the internal diameter of the reaction tube should preferably be observed.

DE-A 27 15 209 discloses a process for preparing 3-alkylbuten-1-als, wherein a catalyst with a total layer thickness of 5 to 35 mm and 2 or more layers of silver and/or copper crystals is used. The production of the catalyst with a plurality of layers is of the noble metal is relatively complex.

EP-A 357 292 discloses a process for preparing ethylene oxide. The catalysts used in this process are silver catalysts, wherein the silver has been applied to a porous heat-resistant support with a particular specific BET surface area. According to the information in this document, the silver can be applied to the support as a suspension of silver or silver oxide in a liquid medium, for example water, or by impregnation of the support with a solution of a silver compound. Subsequently, this silver compound is reduced to elemental silver by thermal treatment. There is no information in this document regarding a possible use of the supported silver catalysts thus prepared for preparing ethylenically unsaturated carbonyl compounds.

3-Methylbut-2-en-1-al, also known by the trivial name prenal, is an important precursor for citral, which is in turn an important product for a multitude of chemical syntheses. The catalysts described in the literature for preparation of prenal (3-methylbut-2-en-1-al) are produced by relatively complex processes and under production conditions which are in need of improvement overall. It would therefore be desirable to obtain supported noble metal catalysts for the synthesis of prenal from isoprenol (3-methylbut-3-en-1-ol), which are obtainable in a simple manner and which can also be controlled with regard to their selectivity simply by additions of compounds which act as promoters.

BRIEF SUMMARY OF THE INVENTION

This object is achieved in accordance with the invention by the use of supported noble metal catalysts which by applying a complexed sparingly soluble compound of a noble metal, optionally in a mixture with additives which act as promoters, to a support material from suspension or solution, and subsequently thermally treating the product obtained in this stage at temperatures in the range from 100 to 400° C. over a period of 5 minutes to 5 hours, for preparing olefinically unsaturated carbonyl compounds from olefinically unsaturated alcohols by oxidative dehydrogenation.

The present invention further relates to a process for producing a supported noble metal catalyst for oxidative dehydrogenation of olefinically unsaturated alcohols, wherein a complexed sparingly soluble compound of a noble metal, optionally in a mixture with additives which act as promoters, is applied to a support material from suspension or solution, and then the product thus obtained is treated thermally at temperatures in the range from 100 to 400° C. over a period of 5 minutes to 5 hours, which forms the elemental noble metal from the noble metal compound by reduction.

The present invention finally relates to supported noble metal catalysts which are obtained by applying a complexed sparingly soluble compound of a noble metal, optionally in a mixture with additives which act as promoters, to a support material from suspension or solution, and subsequently thermally treating the product obtained in this stage at temperatures in the range from 100 to 400° C. over a period of 5 minutes to 5 hours, which have a specific resistivity of not more than 1000 mΩ*m (milliohm meter), preferably of not more than 500 mΩ*m (milliohm meter) and more preferably of not more than 100 mΩ*m (milliohm meter).

A BRIEF DESCRIPTION OF THE FIGURES

DETAILED DESCRIPTION OF THE INVENTION

Figure 1:
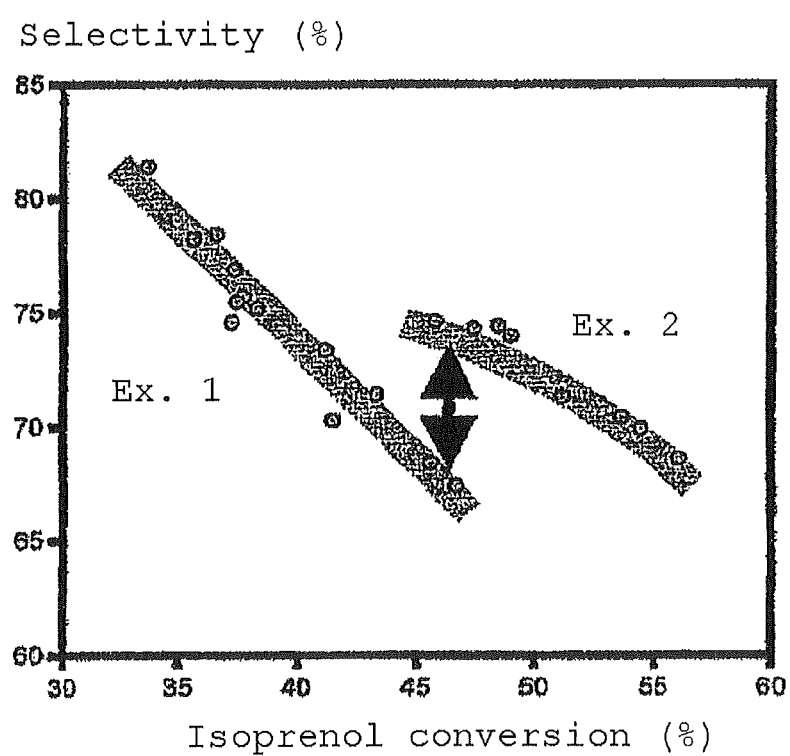
FIG. 1 shows the selectivity as a function of the isoprenol conversion.

The specific resistivity is determined in a test cell, the base of which consists of stainless steel and the casing of which consists of insulating plastic (internal diameter 10 mm, height 32 cm, catalyst volume about 25 ml). The catalyst is introduced and shaken a little in order to obtain a homogeneous catalyst bed. Thereafter, a stainless steel plunger is placed onto the catalyst bed. In this test arrangement, plunger and base serve as test electrodes. To measure the resistivity, a current measuring unit is connected in series with the sample, and a power supply is used to set a voltage between 10 mV and 5 V. The corresponding current is registered and the specific resistivity is calculated. The measurement is carried out at atmospheric pressure and an air humidity of max. 50% at a temperature in the range of 22-25° C.

Preferred embodiments can be inferred from the dependent claims and the description which follows and the examples.

In the inventive use, a supported noble metal catalyst is used, which is obtainable by applying a complexed sparingly soluble compound of a noble metal, optionally in a mixture with additives which act as promoters, to a support material from suspension or solution.

Preference is given to using compounds of the noble metals Cu, Au, Ag, Pd, Pt, Rh, Ru, Ir or Os, and optionally W, or mixtures thereof. The noble metal compounds used are more preferably compounds of Cu and Ag or mixtures thereof. Very particular preference is given to the use of silver compounds.

In the case of use of mixtures, the mixing ratio is not subject to any particular restriction.

The noble metal compounds are present in the suspensions or solutions, from which they are applied to the support material in complexed form, preferably in proportions, calculated as the noble metal, in the range from 0.5 to 50% by weight, preferably in the range from 1 to 40% by weight and more preferably in the range from 5 to 35% by weight.

In principle, suitable compounds of the noble metals mentioned are all of those which have a solubility in aqueous solution at a temperature of 25° C. and a pH of 7 of less than 5.0 g/l, more preferably of less than 1 g/l and more preferably of less than 0.5 g/l. Merely by way of example, compounds of silver mentioned here are silver oxalate, salts of silver with saturated or unsaturated monocarboxylic acids, for example formic acid, acetic acid, propionic acid, butyric acid, lactic acid, or else salts of benzoic acid or salicylic acid. Additionally suitable are compounds of saturated or unsaturated dicarboxylic acids such as fumaric acid or maleic acid, or of saturated or unsaturated tricarboxylic acids, for example citric acid or salts thereof. As mentioned above, suitable compounds in principle are all sparingly soluble compounds of the noble metals, and so the above list should be understood merely as an illustrative is list.

In the inventive use, the sparingly soluble noble metal compounds are contacted in solid form with complexing agents or solutions of complexing agents. Complexing agents preferably include amine-, hydroxyl- and carboxyl-containing hydrocarbons, more preferably chelating compounds with relatively low molecular weight.

Examples of such complexing agents include ammonia, ethylenediamine, mono-, di-, tri- and tetraalkylated ethylenediamines, unsubstituted mono- and diethanolamines, or substituted mono- and diethanolamines, and also triethanolamines. These compounds may additionally have further substitution on the alkyl groups.

Further suitable complexing agents are also amino acids and salts thereof, and in principle cyclic and acyclic compounds which have combinations of one or more amino, hydroxyl or ether functionalities of the general formulae R—O—$R_1$ or $N(R,R_1,R_2)$ (where R=aliphatic or aromatic radical; $R_1$, $R_2$=H, aliphatic or aromatic radical), for example polyalcohols (ethylene glycol, glycerol, polyethylene glycols (PEGs)), and oxo, aza or thio macrocycles.

In a particularly preferred use, the sparingly soluble salts used are oxalates, especially silver oxalate.

The sparingly soluble noble metal compounds are contacted in solid form with the complexing agent or a solution of the complexing agent, which forms a complexed solution or suspension of the sparingly soluble noble metal compound.

It is possible to add further additives suitable as promoters to this solution or suspension of the sparingly soluble noble metal compound. Mentioned merely by way of example here are alkali metals, alkaline earth metals and transition metals (such as Li, Rb, Cs, Ca, Mg, V, Co, Ni, Ir or Re), which can be used, for example, in the form of halides (fluorides, chlorides), carboxylates or nitrates, or else in the form of sulfur-containing anions such as sulfates, sulfites or sulfides. Likewise suitable are phosphates, cyanides and hydroxides, and also carbonates, or mixtures thereof. Finally, it is also possible to use anions of heteropolyacids, especially of heteropolyacids of the elements of the sixth and seventh transition groups of the Periodic Table (notation according to IUPAC proposal of 1985).

In the inventive use, the complexed noble metal compound can be applied to a suitable support material from solution or suspension which may optionally comprise promoters as detailed above.

Suitable support materials are known per se to those skilled in the art and are described in the literature, to which reference is made here for further details.

In a preferred configuration of the present invention, the support materials have minimum porosity and have a BET surface area of not more than 0.1 m$^2$/g.

In a preferred configuration of the present invention, the support materials are spherical and have a mean diameter of 1.3 to 2.5 mm.

Preferred support materials are steatite, aluminum oxides or aluminosilicates.

In some cases, hydrotalcites have also been found to be suitable.

Hydrotalcite is generally understood to mean a layer material with the chemical formula $[M(II)_{1-x}M(III)_x(OH)_2]^{x+}[A_{n/x}]^{n-} * m H_2O$. In this formula, M(II) is a divalent metal, M(III) is a trivalent metal, A is an anion intercollated within the lattice, m is the number of intercollated water molecules and x is the molar ratio of $M(II)/[M(II)+M(III)]$. x is typically within the range from 0.2 to 0.33, which corresponds to molar ratios of M(II) to M(III) in the range from 2 to 4. Examples of divalent metals here include Mg, Fe, Ni, Co, Zn and Mn; examples of trivalent metals include Al, Ga, In, Co and Mn. The possibility of the simultaneous presence of a plurality of divalent or trivalent metals in different molar ratios increases the structural variety of the suitable hydrotalcites.

is Minerals of the hydrotalcite group mentioned here merely by way of example are manasseites, pyroaurite, sjögrenite, stichtite, barbertonite, desautelsite, meixnerite or takovite, which are described in the literature, and the compositions of which are known to those skilled in the art. A preferred hydrotalcite has the composition $Mg_6Al_2(CO_3)(OH)_{16} * 4 H_2O$.

A particularly preferred support material is steatite, a ceramic material based on natural raw materials, which consists of the main component soapstone $(Mg(Si_4O_{10})(OH)_2)$, a natural magnesium silicate. Moreover, additions of clay and feldspar or barium carbonate may be present.

After the application of the sparingly soluble noble metal compound, optionally with the addition of promoters, to the support material from suspension or solution, it is subjected to a thermal treatment at temperatures in the range from 100 to 400° C., preferably from 120 to 360° C. and more preferably from 150 to 340° C. This is effected for a period in the range from 5 minutes to 5 hours, preferably 5 minutes to 3 hours and more preferably 10 minutes to 1 hour.

This thermal treatment forms, from the noble metal compound on the surface of the support material, the noble metal itself, which then constitutes the active species of the supported catalyst.

The noble metal contents, measured in % by weight, based on the support material, after the thermal treatment, are generally in the range from 0.2 to 25% by weight, preferably in the range from 0.5 to 20% by weight and more preferably in the range from 1 to 15% by weight.

In some cases, it has been found to be advantageous, in the event of combination of sparingly soluble noble metal compound and complexing agent, to use a noble metal compound prepared in situ. This process variant is described hereinafter by way of example for the preparation of a sparingly soluble silver compound.

To prepare the sparingly soluble noble metal compounds, it is possible to use any desired salts of these noble metals, in the case of silver, for example, silver nitrate or other silver salts, for example silver sulfate, silver fluoride, silver triflate, silver perchlorate, or else tricyanoargentate or tricyanoargentate compounds.

Additionally suitable are silver starting materials such as silver chloride, silver bromide or silver iodide, silver sulfite or silver carbonate, which can be brought into solution by suitable treatment with acids, for example hydrogen fluoride, nitric acid or sulfuric acid.

The solutions of these salts of the noble metal compounds can then be combined with precipitation reagents in dissolved form, in order to precipitate the sparingly soluble silver compound. In this case, either the precipitation reagent can be added to the silver solution, or the solution of the silver salt to the precipitation reagent. In addition, the precipitation reagent can be used in solid or liquid form, and diluted or undiluted.

The preferred precipitation reagents used in the case of silver may be oxalic acid or salts thereof, which is particularly preferred, saturated or unsaturated monocarboxylic acids such as formic acid or salts thereof, acetic acid or salts thereof, propionic acid or salts thereof, butyric acid or salts thereof or lactic acid or salts thereof.

Likewise suitable are benzoic acid and benzoates and salicylic acid and salts thereof. Mention should additionally be made here of saturated or unsaturated dicarboxylic acids, for example fumaric acid and salts thereof (fumarates) and maleic acid and salts thereof (maleates). Finally, mentioned should also be made of saturated or unsaturated tricarboxylic acids, for example citric acid or salts thereof.

After the precipitation of the sparingly soluble noble metal compound by the procedure described above by way of example for silver, the sparingly soluble noble metal compounds can be isolated from the solution by filtration, filtration using suction filters or other suitable processes, and contacted immediately thereafter with the complexing agent. This process has advantages in the case of sparingly soluble noble metal compounds which have a certain instability or harbor risks when handled. In the case of the preferred use of silver oxalate as the sparingly soluble noble metal compound in the inventive use, the preceding in situ preparation of the oxalate is particularly preferred.

Particularly advantageously, it is possible in accordance with the invention to use the supported noble metal catalysts obtained by the above procedure for the preparation of 3-methylbut-2-en-1-al from 3-methylbut-3-en-1-ol. The product is also known by the trivial name prenal, and the reactant by the trivial name isoprenol.

In the case of this particularly preferred use, the reaction is preferably performed in a tube bundle reactor as described, for example, in EP-A 881 206. For further details of the reactor geometry, reference is made here to this EP-A 881 206 and to EP-A 244 632.

By virtue of the inventive use of the supported noble metal catalysts obtainable as described above, it is possible to obtain prenal from isoprenol under mild thermal conditions with good yield and good selectivity. The conversion of isoprenol with the supported noble metal catalyst obtainable as described above forms a reaction mixture of 3-methylbut-3-en-1-al and 3-methylbut-2-en-1-al. The former isomer mentioned then isomerizes under base catalysis in a subsequent step to give the desired 3-methylbut-2-en-1-al.

In the workup of the reaction mixture, in a first stage, the desired reaction product is separated by distillation from unconverted reactant. In order to be able to perform this distillation in an economically advantageous manner, an azeotrope which consists of 70% 3-methylbut-3-en-1-al and 30% 3-methylbut-2-en-1-al is advantageously utilized. The latter is, as mentioned above, the thermodynamically favored product.

In the inventive use of the supported noble metal catalyst obtainable as described above, prenal can be prepared in good yield at lower temperatures and with good selectivity from isoprenol.

The examples which follow illustrate the advantages of the inventive use.

EXAMPLES 1

Prior Art

Steatite spheres with a diameter of 1.8 to 2.2 mm (manufacturer: Ceram Tec) were coated with silver by the flame spraying process using an acetylene flame (as described by way of example in Army Engineering Manual EM 1110-2-3401). The silver loading of the catalyst after the coating step was 6% by weight. The catalyst thus obtained was tested in a test plant composed of a sandbath-heated quartz glass tubular reactor with internal diameter 13 mm and length 150 mm. For this purpose, the reactor was charged with a bed height of the catalyst of 100 mm. 110 g of evaporated isoprenol and 50 l (STP) [l (STP)=standard liters, the volume of one liter under standard conditions] of air per hour were passed in gaseous form through this catalyst bed.

Figure 2:
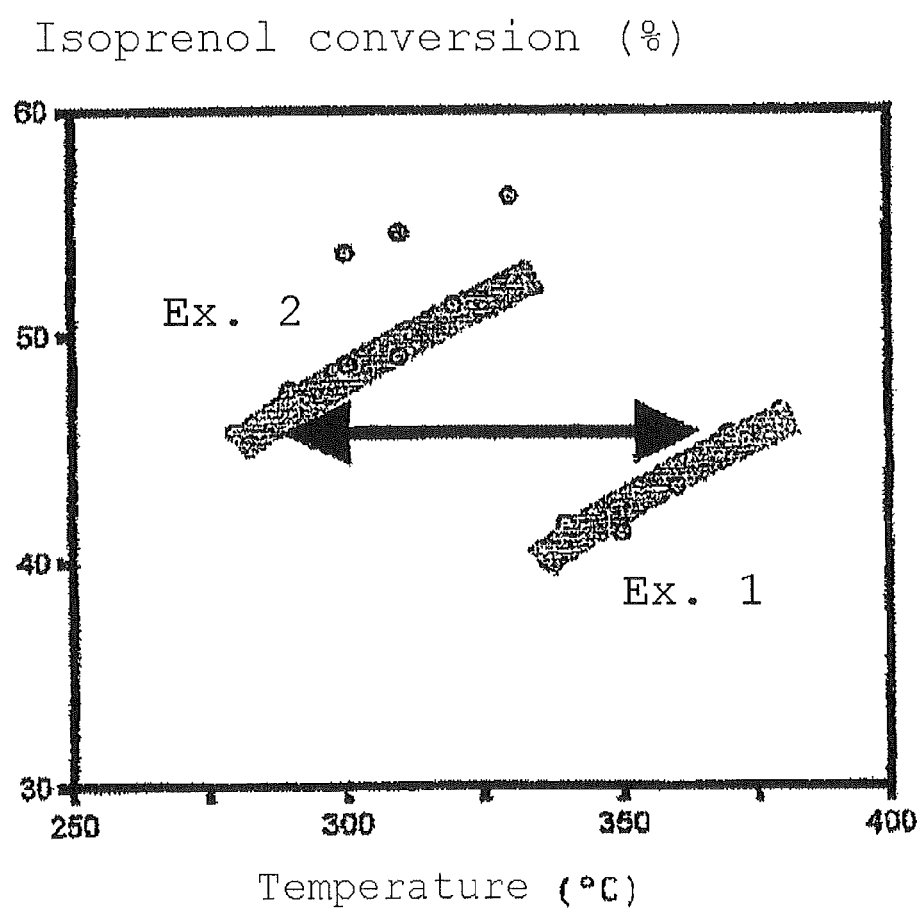
FIG. 2 shows the isoprenol conversion as a function of temperature.

FIG. 1 shows the selectivity as a function of the isoprenol conversion, and FIG. 2 the isoprenol conversion as a function of temperature.

EXAMPLE 2

Steatite spheres with a diameter of 1.5 to 1.8 mm (manufacturer: Ceram Tec) were wetted by applying an ethylenediamine-complexed solution of silver oxalate. The steatite spheres thus wetted with the silver solution were subsequently treated in an air stream at 280° C. for 12 minutes. The specific resistivity of the catalyst thus obtained was 5 mΩ*m.

The catalyst thus obtained was tested for its catalytic action in the test system from example 1. The same bed height and the same throughput of isoprenol and air as in example 1 were used.

FIGS. 1 and 2 compare the selectivity as a function of the isoprenol conversion, and the isoprenol conversion as a function of the temperature of the reactions according to example 1 and example 2.

As clearly evident from FIGS. 1 and 2, an improved catalytic efficacy with regard to selectivity and activity is achieved according to example 2 compared to the catalyst according to example 1.

The invention claimed is:

1. A process for preparing olefinically unsaturated carbonyl compounds from olefinically unsaturated alcohols by oxidative dehydrogenation which comprises utilizing a supported silver catalyst, obtained by a process comprising
   a) applying a complexed sparingly soluble silver compound to a support material from suspension or solution,
   b) subsequently thermally treating the product obtained in stage a) at temperatures in the range from 100 to 400° C. over a period of 5 min to 5 h,
   wherein the complexed sparingly soluble silver compound is complexed with a complexing agent selected from the group consisting of an amine- containing hydrocarbon, a hydroxyl-containing hydrocarbon, a carboxyl-containing hydrocarbon, ammonia, or oxo, aza or thio macrocycle, and
   the sparingly soluble silver compounds used being those having a solubility in aqueous solution at a temperature of 25° C. and a pH of 7 of less than 5.0 g/l.

2. The process according to claim 1, wherein the silver compound is applied in a mixture with additives which act as a promoter.

3. The process according to claim 1,
   wherein 3-methylbut-2-en-1-al is the unsaturated carbonyl compound and is prepared from 3-methylbut-3-en-ol, which is the unsaturated alcohol.

4. A process for producing a supported silver catalyst for oxidative dehydrogenation of olefinically unsaturated alcohols, which comprises
   a) applying a complexed sparingly soluble silver compound to a support material from suspension or solution, and then
   b) thermally treating the product obtained in step a) at temperatures in the range from 100 to 400° C. over a period of 5 min to 5 h,
   which forms the elemental noble metal from the silver compound by reduction,
   wherein the complexed sparingly soluble silver compound is complexed with a complexing agent selected from the group consisting of an amine-containing hydrocarbon, a hydroxyl-containing hydrocarbon, a carboxyl-containing hydrocarbon, ammonia, or oxo, aza or thio macrocycle, and
   the sparingly soluble silver compounds used being those having a solubility in aqueous solution at a temperature of 25° C. and a pH of 7 of less than 5.0 g/l, wherein the support material used is steatite.

5. The process according to claim 4, wherein the silver compound is applied in a mixture with additives which act as promoters.

6. A supported silver catalyst having a specific resistivity of not more than 1000 mΩ*m, obtainable by
   a) applying a complexed sparingly soluble silver compound to a support material from suspension or solution,
   b) subsequently thermally treating the product obtained in step a) at temperatures in the range from 100 to 400° C. over a period of 5 min to 5 h,
   wherein the complexed sparingly soluble silver compound is complexed with a complexing agent selected from the group consisting of an amine-containing hydrocarbon, a hydroxyl-containing hydrocarbon, a carboxyl-containing hydrocarbon, ammonia, or oxo, aza or thio macrocycle, and
   the sparingly soluble silver compounds used being those having a solubility in aqueous solution at a temperature of 25° C. and a pH of 7 of less than 5.0 g/l;
   wherein the support material is steatite.

7. The supported silver catalyst according to claim 6, wherein the silver compound is applied in a mixture with additives which act as promoters.

8. A process for preparing olefinically unsaturated carbonyl compounds from olefinically unsaturated alcohols comprising:
   a) applying a complexed sparingly soluble silver compound to a support material from suspension or solution,
   b) subsequently thermally treating the product obtained in stage a) at temperatures in the range from 100 to 400° C. over a period of 5 min to 5 h to obtain a supported silver catalyst, and
   c) oxidatively dehydrogenating the olefinically unsaturated alcohols utilizing the supported silver catalyst;
   wherein the complexed sparingly soluble silver compound is complexed with a complexing agent selected from the group consisting of an amine-containing hydrocarbon, a hydroxyl-containing hydrocarbon, a carboxyl-containing hydrocarbon, ammonia, or oxo, aza or thio macrocycle, and
   the sparingly soluble silver compounds used being those having a solubility in aqueous solution at a temperature of 25° C. and a pH of 7 of less than 5.0 g/l.

9. The supported silver catalyst according to claim 7, wherein the promoters are alkali metals, alkaline earth metals or transition metals used in the form of halides, carboxylates or nitrates, or in the form of sulfur-containing anions.

10. The process according to claim 5, wherein the promoters are alkali metals, alkaline earth metals or transition metals used in the form of halides, carboxylates or nitrates, or in the form of sulfur-containing anions.

11. The process according to claim 1, wherein the support material is steatite.

12. The process according to claim 8, wherein the support material is steatite.

* * * * *